US012667487B2

(12) United States Patent
Hajishah et al.

(10) Patent No.: US 12,667,487 B2
(45) Date of Patent: Jun. 30, 2026

(54) APPARATUS, SYSTEM AND METHOD OF PROVIDING CUSTOM VACUUM AND ASPIRATION IN A SURGICAL SYSTEM

(71) Applicant: JOHNSON & JOHNSON SURGICAL VISION, INC., Irvine, CA (US)

(72) Inventors: Abraham Hajishah, Irvine, CA (US); Edith W. Fung, Diamond Bar, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 216 days.

(21) Appl. No.: 16/152,247

(22) Filed: Oct. 4, 2018

(65) Prior Publication Data

US 2019/0099528 A1 Apr. 4, 2019

Related U.S. Application Data

(60) Provisional application No. 62/568,237, filed on Oct. 4, 2017.

(51) Int. Cl.
*A61F 9/007* (2006.01)
*A61B 17/00* (2006.01)
(Continued)

(52) U.S. Cl.
CPC ........... *A61F 9/00745* (2013.01); *A61M 1/73* (2021.05); *A61M 1/74* (2021.05); *G16H 40/63* (2018.01);
(Continued)

(58) Field of Classification Search
CPC .......... A61M 1/0031; A61M 2205/078; A61M 2205/50; A61M 2205/502; A61M 1/74;
(Continued)

(56) References Cited

U.S. PATENT DOCUMENTS

| | | | |
|---|---|---|---|
| 4,954,960 A | 9/1990 | Lo et al. | |
| 5,700,240 A | 12/1997 | Barwick, Jr. et al. | |

(Continued)

FOREIGN PATENT DOCUMENTS

| | | |
|---|---|---|
| IN | 201206927 | 11/2015 |
| WO | 2010054146 A1 | 5/2010 |

(Continued)

OTHER PUBLICATIONS

Ngo, W.K., et al., "Heat Profiling of Phacoemulsification Tip Using a Thermal Scanning Camera," International Ophthalmology, Dec. 2013, vol. 33(6), pp. 645-649.

(Continued)

*Primary Examiner* — Philip R Wiest
*Assistant Examiner* — Meagan Ngo

(57) ABSTRACT

An apparatus, system and method for providing a may include at least a phacoemulsification surgical console having a customizable non-linear custom aspiration mode. The console may include at least an aspirator; a foot pedal; and a non-transitory computing code resident on a computing memory associated with a computing processor which, when executed by the processor, causes to be executed the steps of: receiving a percentage actuation of the foot pedal; calculating, including from a non-linear algorithm, a percentage actuation for the aspirator corresponded to the received percentage foot pedal actuation; and dictating the calculated percentage aspirator actuation to the aspirator.

6 Claims, 3 Drawing Sheets

(51) Int. Cl.
    *A61M 1/00*         (2006.01)
    *G16H 40/63*       (2018.01)

(52) U.S. Cl.
    CPC .............. *A61B 2017/00973* (2013.01); *A61B 2017/00977* (2013.01); *A61M 1/77* (2021.05); *A61M 2205/078* (2013.01); *A61M 2205/50* (2013.01); *A61M 2205/502* (2013.01); *A61M 2210/0612* (2013.01)

(58) Field of Classification Search
    CPC ...... A61M 2005/14208; A61F 9/00736; A61F 9/00745; G16H 40/63; G16H 20/40; A61B 2017/00973; A61B 2017/00977; A61B 2017/00176
    See application file for complete search history.

(56)             References Cited

U.S. PATENT DOCUMENTS

| | | | |
|---|---|---|---|
| 7,785,336 B2 | 8/2010 | Staggs | |
| 8,523,812 B2 | 9/2013 | Boukhny et al. | |
| 8,523,813 B2 | 9/2013 | Grispo et al. | |
| 8,758,433 B2 | 6/2014 | Cole et al. | |
| 8,986,290 B2 | 3/2015 | Patton et al. | |
| 2003/0073980 A1* | 4/2003 | Finlay | A61B 17/00 606/1 |
| 2011/0092887 A1* | 4/2011 | Wong | A61B 90/98 604/22 |
| 2011/0092924 A1* | 4/2011 | Wong | G05G 1/445 604/290 |
| 2012/0083800 A1 | 4/2012 | Andersohn et al. | |
| 2012/0302941 A1* | 11/2012 | Teodorescu | A61F 9/00745 604/22 |
| 2014/0276920 A1 | 9/2014 | Hendrick et al. | |
| 2015/0144514 A1 | 5/2015 | Brennan et al. | |
| 2015/0164690 A1* | 6/2015 | Peterson | A61F 9/00736 604/67 |
| 2016/0302816 A1 | 10/2016 | Clayton et al. | |

FOREIGN PATENT DOCUMENTS

| | | |
|---|---|---|
| WO | 2011084221 A2 | 7/2011 |
| WO | 2012161913 A1 | 11/2012 |

OTHER PUBLICATIONS

International Search Report and Written Opinion for Application No. PCT/IB2018/057578, mailed on Dec. 19, 2018, 18 pages.

\* cited by examiner

APPARATUS, SYSTEM AND METHOD OF PROVIDING CUSTOM VACUUM AND ASPIRATION IN A SURGICAL SYSTEM

CROSS REFERENCES TO RELATED APPLICATIONS

This application claims the benefit under 35 U.S.C. § 119(e) of U.S. Provisional Patent Application No. 62/568,237, filed Oct. 4, 2017, which is incorporated herein by reference in its entirety.

BACKGROUND

Field of the Disclosure

The present disclosure relates to medical devices and systems, and, more specifically, to an apparatus, system and method of providing custom vacuum and/or aspiration in a surgical system.

Description of the Background

Phacoemulsification is a medically recognized technique utilized for crystalline lens removal. Phacoemulsification includes making a corneal and/or scleral incision, and the insertion of a phacoemulsification handpiece, which is typically comprised of a needle that is ultrasonically driven in order to emulsify, i.e., to liquefy, the natural crystalline lens and/or an unhealthy aspect, such as a cataract, associated therewith.

The phacoemulsification handpiece is generally coupled to an irrigation source and an aspiration pump. The handpiece includes a distal tip for insertion within the anterior chamber of the patient's eye that emits ultrasonic energy to emulsify the crystalline lens. The handpiece further includes an irrigation port proximal to the distal tip, which is coupled to an irrigation source via an irrigation line, and an aspiration port at the distal tip, which is coupled to an aspiration pump via an aspiration line. Fluid from the irrigation source, which is typically an elevated bottle of saline solution, is irrigated into the eye via the irrigation line and the irrigation port, and the irrigation fluid and emulsified crystalline lens material are aspirated from the eye by the aspiration pump via the aspiration port and the aspiration line.

Other medical techniques for the eye also typically include irrigating the eye and aspirating. Such procedures may or may not include the destruction, alteration or removal of features of the natural eye.

Aspiration is generally achieved with one of a variety of different aspiration pumps known in the art. Two common types of aspiration pumps are: volumetric flow or positive displacement pumps (such as peristaltic or scroll pumps); and vacuum-based pumps (such as venturi, diaphragm, or rotary-vane pumps).

A vacuum-based aspiration pump indirectly controls fluid flow by controlling the vacuum within the fluidic circuit. For example, a venturi pump creates a lower pressure in a drainage cassette reservoir, which causes the fluid to flow from the eye into the aspiration line and into the drainage cassette reservoir. Thus, instead of pushing fluid through the aspiration line like a volumetric flow pump, the fluid is essentially pulled by a vacuum through the line. The rate of fluid flow generated by a vacuum-based pump is generally higher than the rate of fluid flow generated by a volumetric flow based pump, but current systems and methods for controlling the rate of flow for the vacuum-based pump necessitate manual adjustment of the operative vacuum level and are thus imprecise, which causes safety and efficacy concerns.

Moreover, during phacoemulsification in particular, it is possible for the aspirating phacoemulsification handpiece to become occluded by particulate that blocks the aspirating handpiece. For volumetric flow pumps, this blockage can result in increased vacuum. For a vacuum-based pump, this blockage can result in a volumetric fluid flow drop off near the aspiration port. In each case, once the occlusion is cleared, the resulting rush of fluid from the anterior chamber into the aspiration line can outpace the volumetric flow of new fluid into the eye from the irrigation source, which may lead to severe eye trauma.

In order to address the aforementioned safety and efficacy concerns, current methods of vacuum and aspiration deliveries are generally limited to two modes, referred to herein as "panel" and "linear." That is, intermediate adjustments for delivery are not made freely available, in part in order to minimize the need for and risk inherent in manual adjustment.

As to the referenced modes, the "panel" mode typically provides strict, fixed values upon user selection, and the "linear" mode allows only the simplest form of the linear adjustment from 0% to 100%. Yet further, a time lag is generally present in the event of any effort to adjust within a mode. Accordingly, both such modes are slow and inadequate to deal with urgent surgical situations as such situations arise.

Therefore, the need exists for an apparatus, system, and method for providing a custom mode for vacuum and/or aspiration in a surgical system.

SUMMARY

The disclosed apparatus, system and method may include at least a phacoemulsification surgical console having a customizable non-linear custom mode for vacuum and/or aspiration. The console may include at least an aspirator, which may include one or more pumps; a foot pedal; and a non-transitory computing code resident on a computing memory associated with a computing processor which, when executed by the processor, causes to be executed the steps of: receiving a percentage actuation of the foot pedal; calculating, including from a non-linear algorithm, a percentage actuation for the aspirator corresponded to the received percentage foot pedal actuation; and dictating the calculated percentage aspirator actuation to the aspirator.

More particularly, the disclosed method of providing a customizable, non-linear custom mode for vacuum and/or aspiration in ophthalmic surgery may include at least receiving a foot pedal actuation percentage from an ophthalmic surgery console; relationally comparing the foot pedal actuation percentage to a non-linear custom zone algorithm which is calculated from at least one user-indicated set point for aspiration corresponded to a particular one of the foot pedal actuation percentage; and calculating a next one of the aspiration from the custom zone algorithm.

Thus, the disclosed embodiments provide an apparatus, system, and method for providing a custom mode for vacuum and/or aspiration in a surgical system.

BRIEF DESCRIPTION OF THE FIGURES

Referring now to the figures incorporated herein, shown are non-limiting embodiments of the present disclosure, wherein like numerals represent like elements, and wherein.

DETAILED DESCRIPTION

Figure 1:
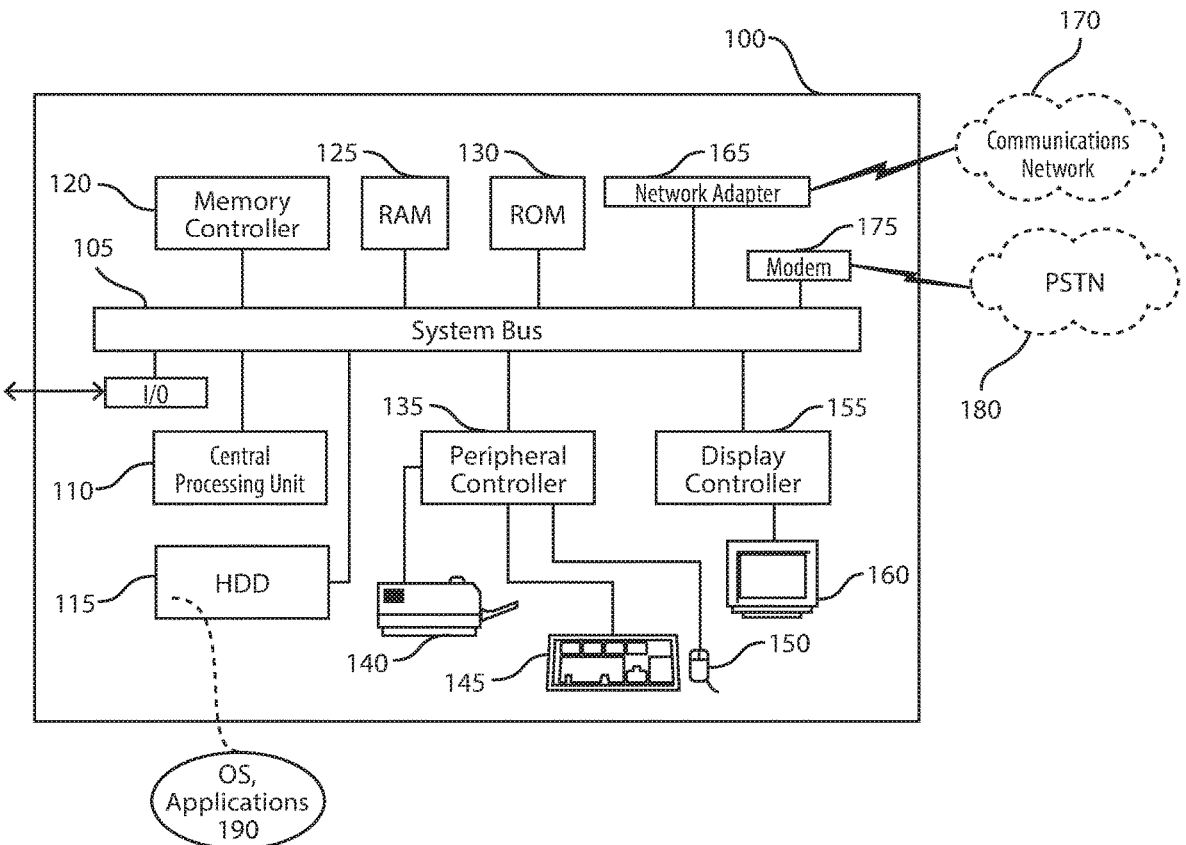
FIG. 1 is a block diagram illustrating a computing system according to the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens with a handpiece. Once the lens is emulsified, it is aspirated from the eye by applying a vacuum tube to the emulsified lens material. During the procedure, irrigation is performed, and aspirated material replaced, using a balanced salt solution, thereby maintaining pressure in the interior of the eye. The emulsified and aspirated lens is then typically replaced with a clear artificial intraocular lens (IOL).

To perform the afore-discussed and similar procedures, a surgeon often utilizes a computer-controlled system of specialized equipment called a phacoemulsification system to control and execute the ultrasonic emulsification and aspiration of the natural lens of the eye prior to inserting the IOL. Phacoemulsification systems use various computer programs for performing these various tasks, which are controlled in part by adjusting settings of these programs to drive motors and pumps, for example, which emulsify and aspirate the subject lens material and which do other tasks necessary to complete the surgery. Different phacoemulsification systems may provide different programs for use in different situations. For example, the program settings selected may take into account the particular subject eye on which surgery is performed based, for example, on measurements of the eye and various other aspects of the patient's physiology.

During the procedure, information such as the amount of vacuum applied to aspirate, the flow rate, a microscopic view of the operating field, and the like, may be displayed on and controllable from a user interface of the phacoemulsification system console, or on a separate screen, computer, or other viewing device, and may be monitored and verbally reported by support staff during the procedure. At least some of this data is commonly used to inform and improve ongoing and subsequent procedures.

FIG. 1 depicts an exemplary computing system 100 for use in association with an ophthalmic surgical console in accordance with herein described system and methods. Computing system 100 is capable of executing software, such as an operating system (OS) and one or more computing applications 190. The operation of exemplary computing system 100 is controlled primarily by computer readable instructions, such as instructions stored in a computer readable storage medium, such as hard disk drive (HDD) 115, optical disk (not shown) such as a CD or DVD, solid state drive (not shown) such as a USB "thumb drive," or the like. Such instructions may be executed within central processing unit (CPU) 110 to cause computing system 100 to perform operations. In many known computer servers, workstations, personal computers, and the like, CPU 110 is implemented in an integrated circuit called a processor.

It is appreciated that, although exemplary computing system 100 is shown to comprise a single CPU 110, such description is merely illustrative, as computing system 100 may comprise a plurality of CPUs 110. Additionally, computing system 100 may exploit the resources of remote CPUs (not shown), for example, through communications network 170 or some other data communications means 180.

In operation, CPU 110 fetches, decodes, and executes instructions from a computer readable storage medium such as HDD 115. Such instructions may be included in software such as an operating system (OS), executable programs, and the like. Information, such as computer instructions and other computer readable data, is transferred between components of computing system 100 via the system's main data-transfer path. The main data-transfer path may use a system bus architecture 105, although other computer architectures (not shown) can be used, such as architectures using serializers and deserializers and crossbar switches to communicate data between devices over serial communication paths. System bus 105 may include data lines for sending data, address lines for sending addresses, and control lines for sending interrupts and for operating the system bus. Some busses provide bus arbitration that regulates access to the bus by extension cards, controllers, and CPU 110. Devices that attach to the busses and arbitrate access to the bus are called bus masters. Bus master support also allows multiprocessor configurations of the busses to be created by the addition of bus master adapters containing processors and support chips.

Memory devices coupled to system bus 105 may include random access memory (RAM) 125 and/or read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode may normally access only memory mapped by its own process virtual address space; in such instances, the program cannot access memory within another process' virtual address space unless memory sharing between the processes has been set up.

In addition, computing system 100 may contain peripheral communications controller and bus 135, which is responsible for communicating instructions from CPU 110 to, and/or receiving data from, peripherals, such as peripherals 140, 145, and 150, which may include printers, keyboards, and/or the surgical elements, such as foot pedals, discussed herein throughout. An example of a peripheral bus is the Peripheral Component Interconnect (PCI) bus.

Display 160, which is controlled by display controller 155, may be used to display visual output and/or presentation generated by or at the request of computing system 100, responsive to operation of the aforementioned computing program. Such visual output may include text, graphics, animated graphics, and/or video, for example. Display 160 may be implemented with a CRT-based video display, an LCD or LED-based display, a gas plasma-based flat-panel display, a touch-panel display, or the like. Display controller 155 includes electronic components required to generate a video signal that is sent to display 160.

Further, computing system 100 may contain network adapter 165 which may be used to couple computing system 100 to external communication network 170, which may include or provide access to the Internet, an intranet, an extranet, or the like. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

Network adaptor 165 may communicate to and from network 170 using any available wired or wireless technologies. Such technologies may include, by way of non-limiting example, cellular, Wi-Fi, Bluetooth, infrared, or the like.

It is appreciated that exemplary computing system 100 is merely illustrative of a computing environment in which the herein described systems and methods may operate, and does not limit the implementation of the herein described systems and methods in computing environments having differing components and configurations. That is to say, the inventive concepts described herein may be implemented in various computing environments using various components and configurations.

Figure 2:
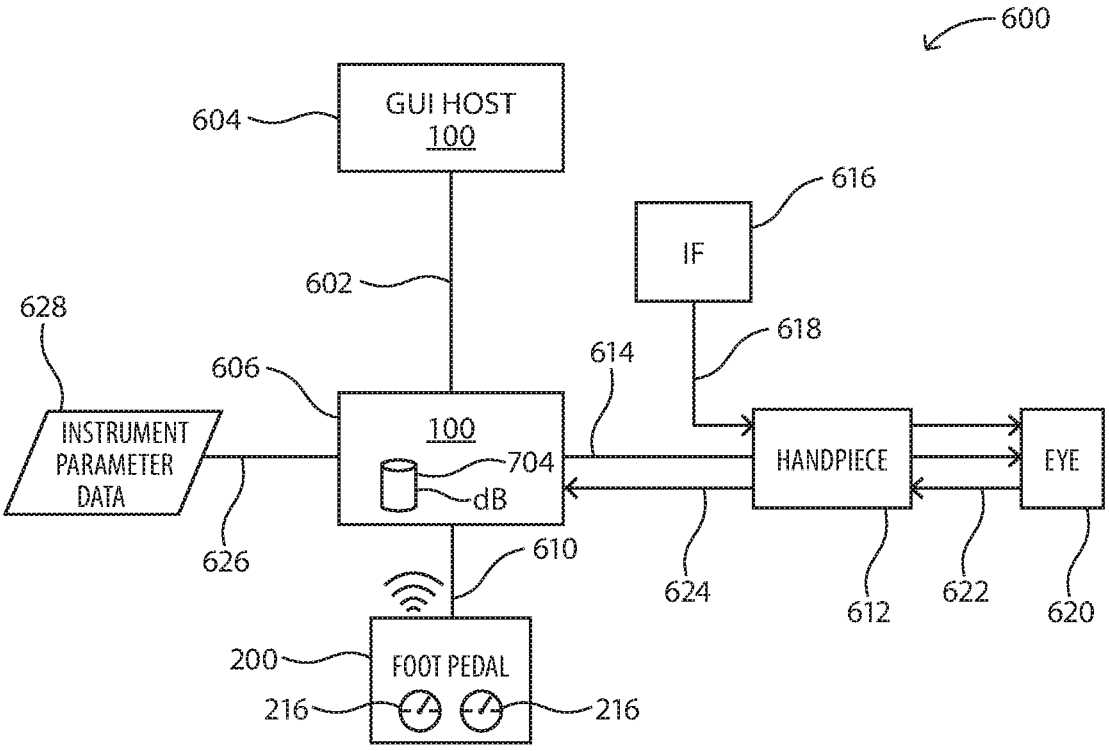
FIG. 2 is a diagram of an ophthalmic surgical console according to the embodiments.

As illustrated in FIG. 2, one peripheral that may communicate using peripheral communications bus 135 is a foot pedal 200. The actuation of the foot pedal 200 by, for example, a user's foot, may have corresponded thereto by the actuation a travel distance, which may be visually indicated on at least one graphical user interface (GUI) 604 of the phacoemulsification system 600 communicatively associated with the foot pedal 200. The system may employ the computer system 100 discussed above, by way of example.

Moreover, the programmable travel positions of the foot pedal 200 may control different functions provided by the console 606, and/or may be additive in functionality. For example, a first travel position for foot pedal 200 may be programmed to have the console 606 provide a specific aspiration function, a second position may add an irrigation function, and a third position may add another function to the aspiration and irrigation function. In addition, other switches 216 may allow for control of the functions activated via the foot pedal 200. For example, if an aspiration function is activated, at least one other switch 216 may be programmed to control the strength of the vacuum applied.

Although the present foot pedal control may be used in various surgical environments and applications, a particularly useful application is in an ocular surgical system, such as a phacoemulsification/vitrectomy system. In an exemplary phacoemulsification system 600, a serial communication cable 602 may connect a GUI 604 and console 606 for the purposes of controlling the console 606 by the GUI host 604. The console 606 may be considered a computational device in the arrangement shown, but other arrangements are possible. A switch module associated with an exemplary foot pedal 200, such as described herein, transmits control signals relating internal physical and virtual switch position information as input to the console 606 over a serial communications cable 610, or wirelessly if desired.

The system 600 has a handpiece 612 that typically includes a needle and electrical means, such as a piezoelectric crystal, for ultrasonically vibrating the needle. The console 606 supplies power on line 614 to the operative tip 612. An irrigation fluid source 616 can be fluidly coupled to operative tip 612 through line 618. The irrigation fluid and ultrasonic power are applied by the operative tip 612 to an eye 620, or other affected area or region. Alternatively, the irrigation source may be routed to the eye 620 through a separate pathway independent of the handpiece. Aspiration is provided from the eye 620 by one or more pumps (not shown), such as a peristaltic pump and/or venturi pump, via the console 606, through lines 622 and 624. A surgeon/operator may select modes of operation of the foregoing, and variables within each mode, via the GUI, using the foot pedal, and/or by voice command, by way of non-limiting example.

An interface communications cable 626 connects to the console 606 for distributing instrument data 628, and may include distribution of instrument settings and parameter information, to other systems, subsystems and modules within and external to console 606. Although shown connected to the console 606, interface communications cable 626 may be connected or realized on any other subsystem (not shown) that could accommodate such an interface device able to distribute the respective data.

The disclosed embodiments may provide at least customizable, non-linear "custom modes" for vacuum and aspiration in ophthalmic surgery, such as for phacoemulsification surgery performed using the foregoing console and foot pedal, for example. More particularly, foot pedal 200 may be used to indicate various custom operations for aspiration/vacuum 622, 624. These custom operations may be corresponded to particular positions for foot pedal 200 in or by the operative program operating on console 606, such as using one or more databases 704 associated with the programming on console 606.

The embodiments may employ an algorithm that encompasses a predetermined number of, such as two, user-defined parameters for the equipment and peripherals associated with console 606. The algorithm calculates a delivery of the vacuum and aspiration tailored to the user's needs and/or preferences based on these user-defined parameters. By way of non-limiting example, this calculation may divide the "delivery zone", such as may be corresponded to operative zones of a foot pedal 200, for the vacuum and aspiration into two sections: the first section gives the user a choice to decide how sharply or gradually to provide the vacuum an d/or aspiration at certain designated gradients; and the second section may provide a "comfort zone" in which the vacuum or aspiration may be applied smoothly, such as linearly, and/or such as within a user-defined slope.

The custom mode or modes may be available in only select, or in all, surgical submodes that use the aforementioned vacuum and aspiration. More particularly, the custom mode or modes may be available in at least Irrigation/Aspiration (IA) submodes provided by GUI 604 on console

606 for phacoemulsification, such as wherein a wide range of foot-pedal actuations of footpedal 200 may be available for said submodes.

The timing between the aforementioned delivery and comfort zones may be defined by the user. For example, the user may select a set of values, such as the foot pedal treadle percentage in a particular zone, such as in "use-zone 2" (hereinafter, variable X) of foot pedal 200 in the examples below, which may then be algorithmically corresponded to a vacuum and/or aspiration percentage of aspiration/vacuum 622, 624 (hereinafter, variable Y) for timing within a certain zone prior to changeover to another zone. That is, the algorithm may interrelate the values X to the values Y based on a set point (X1, Y1), and the function provided by the algorithm may vary in different use zones. Accordingly, the value set may be applied to calculate the slopes and trajectories, i.e., the mathematical function, of the Y values dependent on the X values, which slopes and trajectories may differ upon crossover between the aforementioned delivery and comfort, or any other or additional, zones.

Correspondingly and by way of non-limiting example, the algorithm may interrelate the X value of the physical foot-pedal depression percentage in a given foot pedal use-zone to the Y value of the calculated phacoemulsification vacuum an d/or aspiration level to be applied. Moreover, the functions provided by the algorithm, such as may reside in a computing application 190 associated with database 704 that is associated with console 606, may include certain known modes in certain use-zones, such wherein a linear-step modification to vacuum is provided interstitially between the algorithmically-controlled modes. Additionally, the applied algorithm in a given-use zone may vary as between periods within the zone, such as variations between a start-segment, a performance-segment, and a final-segment.

By way of non-limiting example, two segments may be constructed to obey the following formulas (wherein FP2% is foot pedal treadle zone 2 percentage, X1 is the Start Segment Limit FP2% value defined in the GUI, and Y1 is the Start Segment Limit VAC/ASP % defined in the GUI). By way of example, if Actual FP2% is <=defined as X1, the custom vacuum or aspiration (as indicated by FP2) may be calculated using:

$$\text{New Factor} = (Y1/X1) * FP2\% \qquad \text{Start Segment:}$$

Also by way of non-limiting example, if Actual FP2% is >X1, the custom vacuum or aspiration may be calculated using:

$$\text{New Factor} = [1/(100 - X1)] * [(100 - Y1) * FP2\% + 100 * (Y1 - X1)] \qquad \text{Performance Segment:}$$

Using the New Factor result, the vacuum and/or aspiration for firmware may be calculated as:

$$\text{Firmware Max VAC Value} = \text{New Factor} * \text{Max Vacuum(from GUI)}$$

$$\text{Firmware Max Asp Value} = \text{New Factor} * \text{Max Aspiration(from GUI)}$$

Such a segmented algorithm may account for all existing modes, such as linear, panel and non-zero algorithmic, and may be derived by selecting a set point (X1, Y1) that matches an algorithmic and existing mode for vacuum and/or aspiration.

Table 1, immediately below, illustrates an exemplary variable mode application, wherein a customizable algorithmic mode is included in addition to the known panel and linear modes.

TABLE 1

| Mode | FP Zone 2 Percentage Input | Percentage of Max Vacuum and Aspiration Output | Implementation Status |
|---|---|---|---|
| Panel | 0 < FP2% <= 100 1% to 100% | F(X) = 100 100% | Existing |
| Linear | 0 < FP2% <= 100 1% to 100% | F(X) = X 1% to 100% | Existing |
| Custom Mode Start Segment | 0 < X1 <= 100 0 < FP2% <= X1 | 0 < Y1 <= 100 F(X) = (Y1/X1) * FP2% | New |
| Performance Segment | X1 < FP2% <= 100 | F(X) = [1/(100 − X1)] * [(100 − Y1) * FP2% + 100 * (Y1 − X1)] | |

By way of additional example, using user-defined parameters of 40% vacuum delivery at 5% foot-pedal travel in zone 2, the known use-zone values, i.e., the set point discussed throughout, for X1 and Y1, as assigned by the user, are (5, 40). These values may serve to define therefrom a performance trajectory algorithm from a zone-start value to a zone-end value. This algorithm may then be applied in that use zone, based on the previously defined user values.

Additional non-limiting exemplary embodiments are provided immediately below in Table 2.

TABLE 2

| FP Zone Percentage | Custom Mode Example 1 | Linear | Custom Mode Example 2 | Custom Mode Example 3 | Custom Mode Example 4 | Custom Mode Example 5 | Custom Mode Example 6 |
|---|---|---|---|---|---|---|---|
| 0 | 0 | 0 | 0 | 0 | 0 | 0 | 0 |
| 5 | 16 | 5 | 3.125 | 30 | 100 | 40 | 10 |
| 10 | 32 | 10 | 6.25 | 60 | 100 | 43.157895 | 20 |
| 15 | 48 | 15 | 9.375 | 90 | 100 | 46.315789 | 30 |
| 20 | 64 | 20 | 12.5 | 90.5882353 | 100 | 49.473684 | 40 |
| 25 | 80 | 25 | 15.625 | 91.7647059 | 100 | 52.631579 | 50 |
| 30 | 81.33333333 | 30 | 18.75 | 91.7647059 | 100 | 55.789474 | 60 |
| 35 | 82.66666667 | 35 | 21.875 | 92.3529412 | 100 | 58.947368 | 70 |
| 40 | 84 | 40 | 25 | 92.9411765 | 100 | 62.105263 | 72.3076923 |
| 45 | 85.33333333 | 45 | 31.25 | 93.5294118 | 100 | 65.263158 | 74.6153846 |
| 50 | 86.66666667 | 50 | 37.5 | 94.1176471 | 100 | 68.421053 | 76.9230769 |
| 55 | 88 | 55 | 43.75 | 94.7058824 | 100 | 71.578947 | 79.2307692 |
| 60 | 89.33333333 | 60 | 50 | 95.2941176 | 100 | 74.736842 | 81.5384615 |
| 65 | 90.66666667 | 65 | 56.25 | 95.8823529 | 100 | 77.894737 | 83.8461538 |
| 70 | 92 | 70 | 62.5 | 96.4705882 | 100 | 81.052632 | 86.1538462 |
| 75 | 93.33333333 | 75 | 68.75 | 97.0588235 | 100 | 84.210526 | 88.4615385 |
| 80 | 94.66666667 | 80 | 75 | 97.6470588 | 100 | 87.368421 | 90.7692308 |
| 85 | 96 | 85 | 81.25 | 98.2352941 | 100 | 90.526316 | 93.0769231 |
| 90 | 97.33333333 | 90 | 87.5 | 98.8235294 | 100 | 93.684211 | 95.3846154 |
| 95 | 98.66666667 | 95 | 93.75 | 99.4117647 | 100 | 96.842105 | 97.6923077 |
| 100 | 100 | 100 | 100 | 100 | 100 | 100 | 100 |

Moreover, the start and/or end values may be defined in alternative manners, as will be understood to the skilled artisan in light of the discussion herein. For example, the percentages for the performance trajectory, given the assigned user set point, may be assessed by multiplying the set point up to the existing maximum vacuum/aspiration to obtain a multiplier factor, and then back-calculating the trajectory slope from the set point based on that maximum multiplier.

By way of non-limiting example only, the following Table 3 provides a comparison between existing panel and linear modes and an exemplary custom mode. For the illustrated exemplary custom mode, the maximum vacuum and aspiration may be provided as set points of 200 mmHg and 40 ccm, respectively.

TABLE 3

| FP Zone 2 | Panel | Linear | Custom |
|---|---|---|---|
| 2% | VAC = 200 mmHg ASP = 40 ccm | VAC = 4 mmHg ASP < 1 ccm | VAC = 32 mmHg ASP = 6 ccm |
| 5% | VAC = 200 mmHg ASP = 40 ccm | VAC = 10 mmHg ASP = 2 ccm | VAC = 80 mmHg ASP = 16 ccm |

TABLE 3-continued

| FP Zone 2 | Panel | Linear | Custom |
|---|---|---|---|
| 10% | VAC = 200 mmHg ASP = 40 ccm | VAC = 20 mmHg ASP = 4 ccm | VAC = 86 mmHg ASP = 17 ccm |
| 50% | VAC = 200 mmHg ASP = 40 ccm | VAC = 100 mmHg ASP = 20 ccm | VAC = 136 mmHg ASP = 27 ccm |
| 80% | VAC = 200 mmHg ASP = 40 ccm | VAC = 160 mmHg ASP = 32 ccm | VAC = 174 mmHg ASP = 35 ccm |
| 90% | VAC = 200 mmHg ASP = 40 ccm | VAC = 180 mmHg ASP = 36 ccm | VAC = 186 mmHg ASP = 37 ccm |

As illustrated in Table 3, above, known linear modes for vacuum and aspiration may exhibit poor performance at the lower aspect of foot-pedal zone 2, while the exemplary custom mode of Table 3 m a y provide sensible reactivity and a tailored linear trajectory throughout its range, including in the zone in which the linear mode underperforms. For example, when FP Zone2 (FP2) is over 50%, the illustrated custom mode may perform comparably to or better than the illustrated linear mode.

The skilled artisan will appreciate, in light of the discussion herein, that the disclosed methods and systems may employ more than one user-defined or system-limitation set point. These multiple set points may relate to either or both of aspiration and vacuum, and may result in two or more use-zone segments within a use-zone, and/or two or more use-zones.

Additionally, in phacoemulsification systems, custom modes may b e used for purposes beyond strict in-surgery use-zones. By way of non-limiting example, custom vacuum and aspiration modes may also be used to apply pump ramp and base power deliveries.

Figure 3:
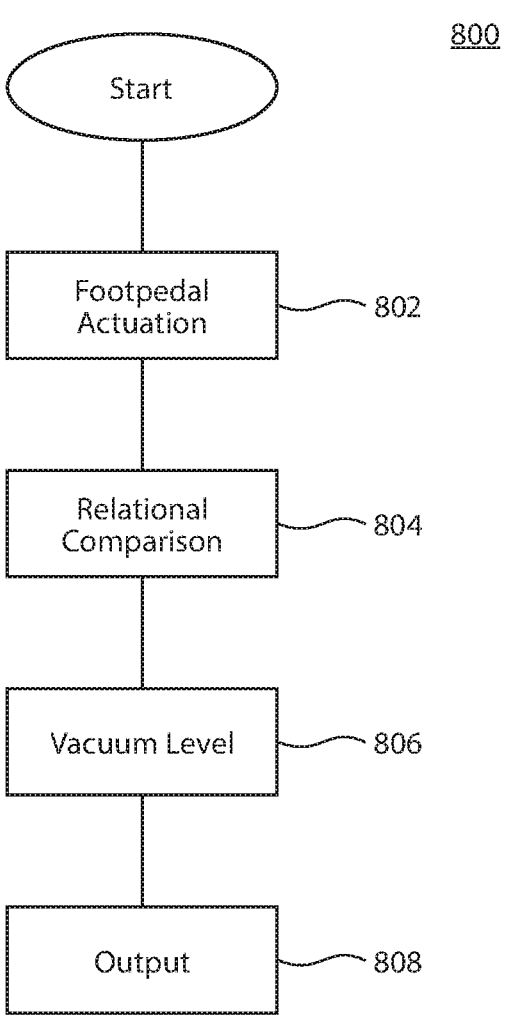
FIG. 3 is a flow diagram of a method according to the embodiments.

FIG. 3 is a flow diagram illustrating a method 800 of providing a customizable, non-linear "custom mode" for vacuum and aspiration in ophthalmic surgery. In order to complement the hardware with customized algorithms (as discussed above) the user may have control of vacuum and aspiration levels. For example, at step 802, a foot pedal actuation percentage is received. At step 804, the foot pedal actuation percentage is compared relationally to a custom zone algorithm, which is calculated from at least one user-indicated set point for aspiration corresponded to particular foot pedal actuation percentages, and which is used to calculate a particular aspiration level for a foot pedal actuation percentage within the zone. At step 806, a foot pedal actuation percentage assessed as being in the custom zone is used by the algorithm for the custom zone to dictate a vacuum level for the surgery. At step 808, the dictated vacuum level is output by the surgical console.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A phacoemulsification surgical console having a customizable non-linear aspiration mode, comprising:

an aspirator comprising at least one of a positive displacement pump and a vacuum-based pump;

a foot pedal; and non-transitory computing code resident on a computing memory associated with a computing processor which, when executed by the processor, causes the execution of the steps of:

receiving by the processor a percentage actuation of the foot pedal;

calculating, including from a non-linear algorithm, based on user definable parameters to customize a percentage actuation for the aspirator corresponding to the received percentage foot pedal actuation; and dictating the calculated percentage actuation to the aspirator to control an aspiration level, wherein:

the calculating from the non-linear algorithm, comprises a start segment calculation, a performance-segment calculation, and a final-segment calculation, wherein the start segment calculation obeys:

$$Y=(Y1/X1)*X$$

wherein Y is the calculated percentage aspirator actuation, X is the percentage foot pedal actuation, X1 is a percentage foot pedal set point, and Y1 is an aspiration percentage set point corresponded to X1.

2. The phacoemulsification console of claim 1, wherein the executed steps further comprise assessing, based on the received foot pedal actuation percentage, a desired operational zone.

3. The phacoemulsification console of claim 2, wherein, based on the assessed operational zone being a first operational zone, the dictating the calculated percentage actuation to the aspirator comprises dictating the calculated percentage actuation from the non-linear algorithm.

4. The phacoemulsification console of claim 3, wherein, based on the assessed operational zone being a second operational zone, the dictating the calculated percentage actuation comprises dictating a linear aspirator percentage actuation.

5. The phacoemulsification console of claim 4, wherein, based on the assessed operational zone being a third operational zone, the dictating the calculated percentage actuation comprises dictating a zero aspirator percentage actuation.

6. The phacoemulsification console of claim 1, wherein the performance segment calculation obeys:

$$Y=[1/(100-X1)]*[(100-Y1)*X+100*(Y1-X1)].$$

* * * * *